(12) United States Patent
Reddy et al.

(10) Patent No.: US 10,550,135 B2
(45) Date of Patent: Feb. 4, 2020

(54) SILICON INCORPORATED QUINOLINES WITH ANTI-MALARIAL AND ANTI-TOXOPLASMOSIS ACTIVITY

(71) Applicant: Council of Scientific & Industrial Research, New Delhi (IN)

(72) Inventors: Dumbala Srinivasa Reddy, Pune (IN); Dhanasekaran Shanmugam, Pune (IN); Remya Ramesh, Pune (IN); Anurag Shukla, Pune (IN); Meenakshi Anil Belekar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/088,695

(22) PCT Filed: Mar. 30, 2017

(86) PCT No.: PCT/IN2017/050118
§ 371 (c)(1),
(2) Date: Sep. 26, 2018

(87) PCT Pub. No.: WO2017/168448
PCT Pub. Date: Oct. 5, 2017

(65) Prior Publication Data
US 2019/0112321 A1    Apr. 18, 2019

(30) Foreign Application Priority Data
Mar. 30, 2016   (IN) .............................. 201611011070

(51) Int. Cl.
*A61K 31/695* (2006.01)
*C07F 7/08* (2006.01)
*A61P 33/06* (2006.01)
*C07D 413/10* (2006.01)

(52) U.S. Cl.
CPC ............ *C07F 7/0816* (2013.01); *A61P 33/06* (2018.01); *C07D 413/10* (2013.01)

(58) Field of Classification Search
CPC .. A61K 31/695; C07D 413/14; C07D 417/14; C07F 7/0816
USPC ................................................. 514/63; 544/1
See application file for complete search history.

(56) References Cited

U.S. PATENT DOCUMENTS

| | | |
|---|---|---|
| 4,492,704 A | 1/1985 | Fleisch et al. |
| 6,809,097 B1 | 10/2004 | Thomas et al. |
| 2009/0312313 A1 | 12/2009 | Shimizu et al. |

FOREIGN PATENT DOCUMENTS

| | | |
|---|---|---|
| CA | 2918888 A1 | 1/2015 |
| WO | 2006117552 A1 | 11/2006 |
| WO | 2007146824 A2 | 12/2007 |
| WO | 2009036412 A1 | 3/2009 |

OTHER PUBLICATIONS

Harker et al., "Toxoplasma gondii dissemination: a parasite's journey through the infected host", Parasite Immunology, 2015, 37, pp. 141-149.
Moll et al., "Methods in Malaria Research", Fifth Edition, MR4 / ATCC, Manassas, Virginia and BioMalPar, Paris, France, 2008, pp. 1-330.
International Search Report and Written Opinion pertaining to International Application No. PCT/IN2017/050118, dated Aug. 1, 2017, 9 pages.
Li, et. al., "Synthesis, Characterization, and Pharmacological Evaluation of Silicon-Containing Aminoquinoline Organometallic Complexes As Antiplasmodial, Antitumor, and Antimycobacterial Agents", Organometallics, vol. 32, Dec. 31, 2012, pp. 141-150, XP002772649, Scheme 1, compound 1 and 2, tables 3 and 4, 10 pages.
Li, et. al., "Synthesis and Evaluation of a Carbosilane Congener of Ferroquine and Its Corresponding Half-Sandwich Ruthenium and Rhodium Complexes for Antiplasmodial and B-Hematin Inhibition Activity", Organometallics, vol. 33, Aug. 18, 2014, pp. 4245-4248, XP002772650, scheme 1, figure 1, 4 pages.
Dahal, et al., "Comparative Study of the Affinity and Metabolism of Type I and Type II Binding Quinoline Carboxamide Analogues by Cytochrome P450 3A4", J. Med. Chem., vol. 55, Nov. 16, 2011, pp. 280-290, XP002772651, scheme 3, step c), figure 3 for R1 substituents, 11 pages.
Foley, et al., "Quinoline Antimalarials: Mechanisms of Action and Resistance and Prospects for New Agents", Pharmacol. Ther., vol. 79, No. 1, 1998, pp. 55-87, XP002772652, figure 1, 33 pages.

*Primary Examiner* — Jeffrey H Murray
(74) *Attorney, Agent, or Firm* — Dinsmore & Shohl, LLP

(57) ABSTRACT

The present invention discloses a silicon incorporated quinoline of formula (I) wherein, X, Y, A, $R^1$ and $R^2$ are as described. The present invention further discloses a process for the preparation of silicon incorporated quinolines of formula I; a pharmaceutical composition comprising silicon incorporated quinolines of formula (I) or pharmaceutically acceptable salt thereof. The present invention also discloses a method for treating diseases caused by *Plasmodium falciparum* or other coccidian parasites using the silicon incorporated quinolines of formula I or pharmaceutically acceptable salt thereof.

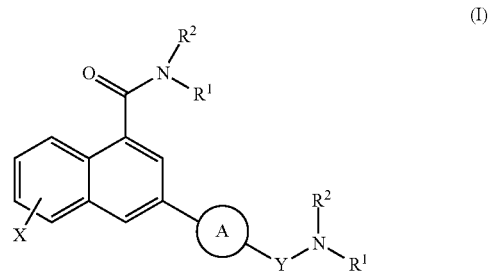

11 Claims, No Drawings

SILICON INCORPORATED QUINOLINES WITH ANTI-MALARIAL AND ANTI-TOXOPLASMOSIS ACTIVITY

FIELD OF THE INVENTION

The present invention relates to a compound of formula I. More particularly, the present invention relates to a silicon incorporated quinoline of formula I and a process for preparation thereof. Further, the present invention also provides a pharmaceutical composition comprising silicon incorporated quinolines of formula I and the use of the silicon incorporated quinoline of formula I for treatment of malaria and toxoplasmosis.

BACKGROUND AND PRIOR ART OF THE INVENTION

Malaria is an infectious disease caused by the protozoan parasites belonging to *Plasmodium* genus and is transmitted to mammalian hosts through the bite of infected mosquitoes. Four species of *Plasmodium* are pathogenic in humans: *P. vivax, P. malariae, P. ovale*, and *P. falciparum*. Several other species of *Plasmodium* infect animals. According to the latest report from WHO, 214 million cases of malaria were reported in 2015 and led to 438000 deaths. Since, malaria is concentrated in countries with comparatively low national income; the cost of malaria treatment is disproportionately borne by the most resource-constrained countries. Although treatment is available, the development of drug resistance poses a big problem in current malaria treatment. Resistance to artemisinins has now been detected in five countries. The most severe neurological complication of malarial infection is cerebral malaria. It is fatal if untreated and is considered as a leading cause of neuro-disability in African children.

The parasitic protozoan *Toxoplasma gondii* is the etiologic agent for toxoplasmosis, a parasitic disease widespread among various warm-blooded animals. Treatment options for *Toxoplasma* include antibiotics such as clindamycin or pyrimethamine/sulphadoxin combination, but the effectiveness of these against the cyst form of the parasite in still not clear and hence it is quite difficult to clear infection completely from infected individuals. It is estimated that ~30% of the global population is infected by this pathogen, and is transmitted via the oral route by consumptions of contaminated food and water. When mammalian hosts eat infected food (rare cooked meat in case of humans), or drink oocysts contaminated water, they acquire the infection [Harker K S, Ueno N, Lodoen M B. *Toxoplasma gondii* dissemination: a parasite's journey through the infected host. Parasite Immunol. 2015, 37(3): 141-9]. Clinical symptoms associated with *Toxoplasma* infection vary from severe (congenital encephalopathy in neonates) to mild (self limiting fever in healthy adults). Recent reports have also suggested that chronic toxoplasmosis in humans can result in altered neurological functions due to the presence of cyst form of the parasite in brain.

WO 2006117552 A1 discloses compound of formula (IA) or (IB), or a salt, N-oxide, hydrate or solvate thereof:

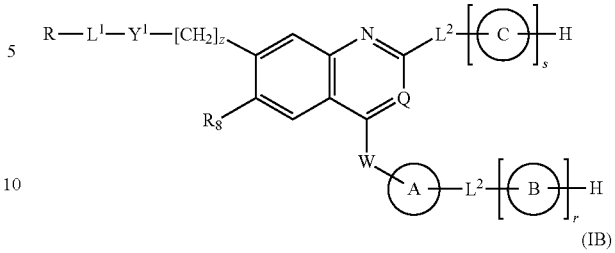

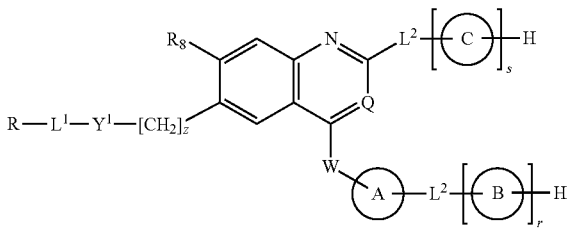

Wherein, $Y^1$ is a bond, —C(=O)—, —S(=O)$_2$—, —C(O)O—, —C(O)NR$_3$—, —C(=S)NR$_3$, —C(=NH)NR$_3$ or —S(O)$_2$NR$_3$— wherein R$_3$ is hydrogen or optionally substituted $C_1$-$C_6$ alkyl; $L^1$ is a divalent radical of formula -(Alk$^1$)$_m$(Q$^1$)$_n$(Alk$^2$)$_p$- wherein m, n and p are independently 0 or 1, Q$^1$ is (i) an optionally substituted divalent mono- or bicyclic carbocyclic or heterocyclic radical having 5-13 ring members, or (ii), in the case where p is 0, a divalent radical of formula -Q$^2$-X$^2$— wherein $X^2$ is O—, —S— or NR$^4$— wherein R$^4$ is hydrogen or optionally substituted $C_1$-$C_3$ alkyl, and Q$^2$ is an optionally substituted divalent mono- or bicyclic carbocyclic or heterocyclic radical having 5-13 ring members, Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^4$—) link wherein R$^4$ is hydrogen or optionally substituted $C_1$-$C_3$ alkyl; z is 0 or 1; R$_6$ is $C_1$-$C_4$ alkoxy, hydrogen or halo; W represents a bond, —CH$_2$—, O, S, S(=O)$_2$—, or —NR$_5$— where R$_5$ is hydrogen or $C_1$-$C_4$ alkyl; Q is =N—, =CH— or =C(X$^1$)— wherein $X^1$ is cyano, cyclopropyl or halo; each $L^2$ independently represents a radical of formula ~(Alk$^3$)$_a$-Z-(Alk$^4$)$_b$- wherein a and b are independently 0 or 1; Alk$^3$ and Alk$^4$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^4$—) link wherein R$^4$ is hydrogen or optionally substituted $C_1$-$C_3$ alkyl; Z represents a bond or an —O—, —S—, —S(=O)$_2$—, —C(=O)—, —NR$^B$—, —CONR$^B$—, —NR$^6$CO—, —SO$_2$NR$^6$—, NR$^6$SO$_2$—, —NR$^6$CONR$^6$— or —NR$^6$CSNR$^6$— radical, wherein R$^6$ is hydrogen or $C_1$-$C_3$ alkyl;

r and s are independently 0 or 1; and rings A, B and C are mono- or bi-cyclic carbocyclic or heterocyclic rings or ring systems having up to 12 ring atoms;

R is a radical of formula (X) or (Y):

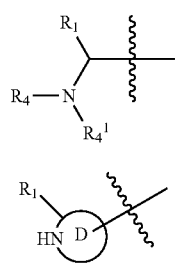

Wherein Ri is a carboxylic acid group (—COOH), or an ester group which is hydrolysable by one or more intracellular carboxylesterase enzymes to a carboxylic acid group; $R_4$ is hydrogen; or optionally substituted $C_1$-$C_6$ alkyl, $C_3$-$C_7$ cycloalkyl, aryl, aryl(d-$C_6$ alkyl)-, heteroaryl, heteroaryl ($C_rC_6$ alkyl)-, —(C=O)$R_3$, —(C=O)O$R_3$, or —(C=O)N$R_3$ wherein $R_3$ is hydrogen or optionally substituted (Ci-$C_6$)alkyl, $C_3$-$C_7$ cycloalkyl, aryl, 317!($C_1$-$C_6$ alkyl)-, heteroaryl, or heteroaryl(Cr$C_6$ alkyl)-; $R_4^1$ is hydrogen or optionally substituted $C_1$-$C_6$ alkyl; and D is a monocyclic heterocyclic ring of 5 or 6 ring atoms wherein $R_1$ is linked to a ring carbon adjacent the ring nitrogen shown, and ring D is optionally fused to a second carbocyclic or heterocyclic ring of 5 or 6 ring atoms in which case the bond shown intersected by a wavy line may be from a ring atom in said second ring.

CA 2918888 A1 discloses compound represented by general formula I, has a strong Ax1 inhibiting activity by introducing a distinctive bicyclic structure in which a saturated carbocyclic ring is fused to a pyridone ring, and thus may be used as a therapeutic agent for Ax1 related diseases such as acute myeloid leukemia, melanoma, breast cancer, pancreatic cancer, cancer such as glioma, kidney disease, immune system disease, and circulatory system disease. Further, it discloses that L is —CO—.

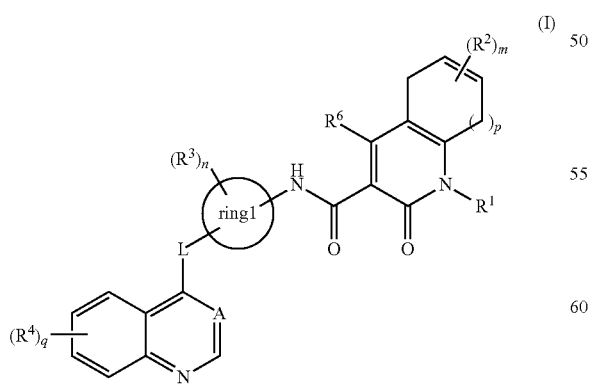

US 20090312313 A1 provides compounds represented by formula (I) and pharmaceutically acceptable salts and solvates thereof:

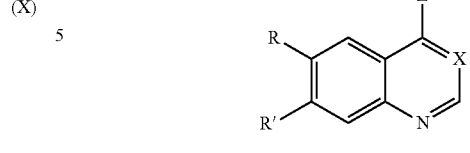

wherein X represents CH or N; Z represents —O—, —NH— or —C(=O)—; R and R' represent a hydrogen atom, hydroxyl, a halogen atom, optionally substituted alkyl, optionally substituted alkenyl optionally substituted alkoxy, amino, aminocarbonyl, or an optionally substituted heterocyclic group; and A represents an optionally substituted specific carbocyclic or heterocyclic group. The compounds according to the present invention have excellent TGFβ inhibitory activity.

WO 2007146824 A2 discloses compounds of Formula (I), and stereoisomers, geometric isomers, tautomers, solvates, metabolites, salts and pharmaceutically acceptable prodrugs thereof, are useful for inhibiting receptor tyrosine kinases and for treating hyperproliferative disorders mediated thereby. Methods of using compounds of Formula (I), and stereoisomers, geometric isomers, tautomers, solvates and pharmaceutically acceptable salts thereof, for in vitro, in situ, and in vivo diagnosis, prevention or treatment of such disorders in mammalian cells, or associated pathological conditions are disclosed.

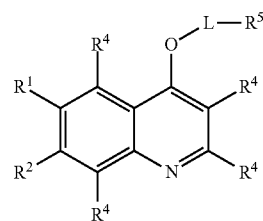

U.S. Pat. No. 6,809,097 B1 discloses compounds of the formula (I):

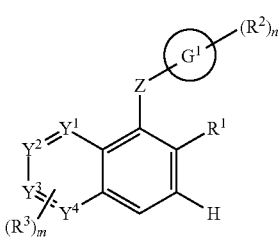

wherein: $R^2$ represents hydroxy, halogeno, $C_{1-3}$alkyl, $C_{1-3}$alkoxy, $C_{1-3}$alkanoyloxy, trifluoromethyl, cyano, amino or nitro; n is an integer from 0 to 5; Z represents —O—, —NH—, —S— or —CH$_2$—; $G^1$ represents phenyl or a 5-10 membered heteroaromatic cyclic or bicyclic group; $Y^1$, $Y^2$, $Y^3$ and $Y^4$ each independently represents carbon or nitrogen; $R^1$ represents fluoro or hydrogen; m is an integer from 1 to 3; $R^3$ represents hydrogen, hydroxy, halogeno, cyano, nitro, trifluoromethyl, $C_{1-3}$ alkyl, —NR$^4$R$^5$ (wherein R$^4$ and R$^5$, can each be hydrogen or $C_{1-3}$alkyl), or a group $R^6$—$X^1$— wherein $X^1$ represents —$CH_2$— or a heteroatom linker group and $R^6$ is an alkyl, alkenyl or alkynyl chain optionally substituted by for example hydroxy, amino, nitro, alkyl, cycloalkyl, alkoxyalkyl, or an optionally substituted group selected from pyridone, phenyl and a heterocyclic ring, which alkyl, alkenyl or alkynyl chain may have a heteroatom linker group, or $R^6$ is an optionally substituted group selected from pyridone, phenyl and a heterocyclic ring and salts thereof, in the manufacture of a medicament for use in the production of an antiangiogenic and/or vascular permeability reducing effect in warm-blooded animals such as humans, processes for the preparation of such derivatives, pharmaceutical compositions containing a compound of formula I or a pharmaceutically acceptable salt thereof as active ingredient and compounds of formula I. The compounds of formula I and the pharmaceutically acceptable salts thereof inhibit the effects of VEGF, a property of value in the treatment of a number of disease states including cancer and rheumatoid arthritis.

WO 2009036412 A1 relates to modulators of ATP-Binding Cassette ('ABC') transporters or fragments thereof, including Cystic Fibrosis Transmembrane Conductance Regulator, compositions thereof, and methods therewith. The present invention also relates to methods of treating ABC transporter mediated diseases using such modulators.

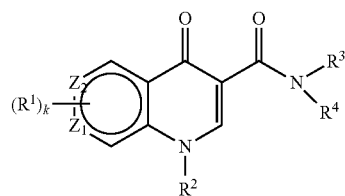

U.S. Pat. No. 4,492,704 A relates to a class of quinoline quinones, which are useful for the therapy of immediate hypersensitivity reactions, such as asthma, and in treating any condition characterized by excessive release of leukotrienes. This patent also includes a method for treating these conditions, which comprises administering to animals, including humans, an effective dose of the quinoline quinone compounds. A further part of this patent is pharmaceutical formulations containing these pharmacologically-active compounds.

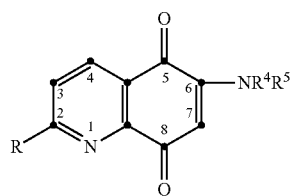

Article titled, "Synthesis, Characterization, and Pharmacological Evaluation of Silicon-Containing Aminoquinoline Organometallic Complexes As Antiplasmodial, Antitumor, and Antimycobacterial Agents" by Yiqun Li, Carmen de Kock, Peter J. Smith, Hajira Guzgay, Denver T. Hendricks, Krupa Naran, Valerie Mizrah, Digby F. Warner, Kelly Chibale, and Gregory S. Smith in *Organometallics*, 2013, 32 (1), pp 141-150 reports two silicon-containing analogues (1, 2) of chloroquine, modified in the lateral side chain with organosilicon moieties, were synthesized. Compounds 1 and 2 were further reacted with dinuclear half-sandwich transition metal precursors $[Ru(Ar)(\mu-Cl)Cl]_2$ (Ar=$\eta^6$-$p$-$^i$PrC$_6$H$_4$Me; $\eta^6$-C$_6$H$_6$; $\eta^6$-C$_6$H$_5$OCH$_2$CH$_2$OH), [Rh(COD)($\mu$-Cl)]$_2$, and [RhCp*($\mu$-Cl)Cl]$_2$, to yield a series of neutral mononuclear Ru(II), Rh(I), and Rh(III) silicon-aminoquinoline complexes (3-12). Compounds 1 and 2 act as monodentate donors that coordinate to the transition metals via the quinoline nitrogen of the aminoquinoline scaffold. Furthermore, the in vitro pharmacological activities of compounds 1-12 were established against chloroquine-sensitive (NF54) and chloroquine-resistant (Dd2) strains of the malarial parasite *Plasmodium falciparum* and against the pathogenic bacterium *Mycobacterium tuberculosis* H$_{37}$R$_v$, as well as an esophageal (WHCO1) cancer cell line.

The search for new anti-malarial drugs is still in progress. However, the hope that new drugs would help eradicate the disease has not been realized. Accordingly, there is a need in the art for new treatments for effectively combating malaria, and particularly malarial forms that are resistant to current treatments, but without the side-effects and complications of drugs and treatments that are presently available. Also there is an urgent need for new and effective drugs for treating and preventing chronic toxoplasmosis.

Objects of the Invention

The main objective of the present invention is to provide a silicon incorporated quinoline of formula I.

Another objective of the present invention is to provide a process for the preparation of silicon incorporated quinoline of formula I.

Yet another objective of the present invention is to provide a pharmaceutical composition comprising silicon incorporated quinoline of formula I or a pharmaceutically acceptable salt thereof and at least one pharmaceutically acceptable carrier.

Still another objective of the present invention is to provide a method for treating diseases caused by *Plasmodium falciparum* or other coccidian parasites, wherein said method comprises administering to the subject a therapeutically effective amount of silicon incorporated quinoline of formula I or pharmaceutically acceptable salt thereof.

SUMMARY OF THE INVENTION

Accordingly, the present invention provides a silicon incorporated quinoline of formula I;

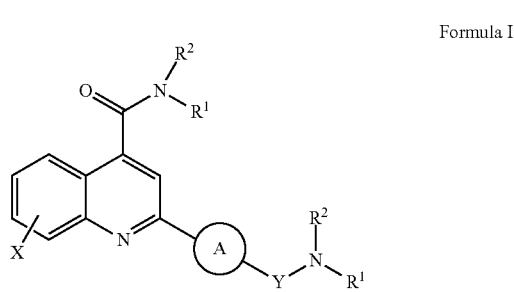

Formula I wherein,
X is selected from the group consisting of hydrogen, halogen, $C_1$-$C_5$ alkyl, $C_1$-$C_5$ haloalkyl, $C_1$-$C_5$ hydroxyalkyl, $C_1$-$C_5$ thioalkyl and $C_1$-$C_5$ alkoxy;
Y is $CH_2$ or absent;

A is selected from the group consisting of

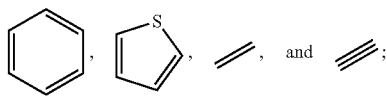

R¹ and R² are independently selected from the group consisting of hydrogen, $C_1$ to $C_{12}$ alkyl, $C_1$-$C_5$ aryl, $C_1$-$C_5$ heteroaryl, $C_1$-$C_5$ aralkyl, $C_1$-$C_5$ hydroxyalkyl, $C_1$-$C_5$ alkoxyalkyl and $C_1$-$C_5$ aminoalkyl which is optionally substituted or forms a 5-6 membered ring which optionally contains an additional hetero atoms selected from the group consisting of O, S, N and Si; and R¹ or R² essentially comprises at least one silicon atom.

In another embodiment, the present invention provides a process for the preparation of silicon incorporated quinoline of formula I, wherein said process comprising the steps of:

a) adding an amino compound, a base to a solution of 4-(bromomethyl)benzonitrile in a solvent followed by stirring at temperature in the range of 25 to 30° C. for a period in the range of 10 to 12 h to obtain corresponding cyano compound 1 or compound 4;

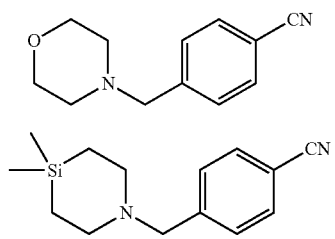

b) refluxing a reaction mixture of a Grignard reagent and a solution of compound 1 or compound 4 obtained in step (a) in a solvent at a temperature in the range of 100 to 110° C. for a period in the range of 3 to 4 hrs followed by cooling to 0° C. and acidifying with an acid and further refluxing at a temperature in the range of 100 to 110° C. for a period in the range of 1 to 2 h to obtain corresponding keto compound 2 or compound 5;

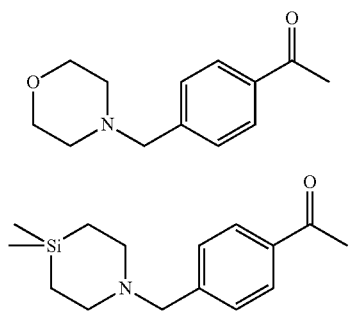

c) adding a solvent followed by a base to a reaction mixture of compound 2 or compound 5 obtained in step (b) and 5-fluoroisatin followed by heating the reaction mixture at a temperature in the range of 110 to 120° C. for a period in the range of 10 to 20 min in a microwave reactor to obtain corresponding acid compound 3 or compound 6; and

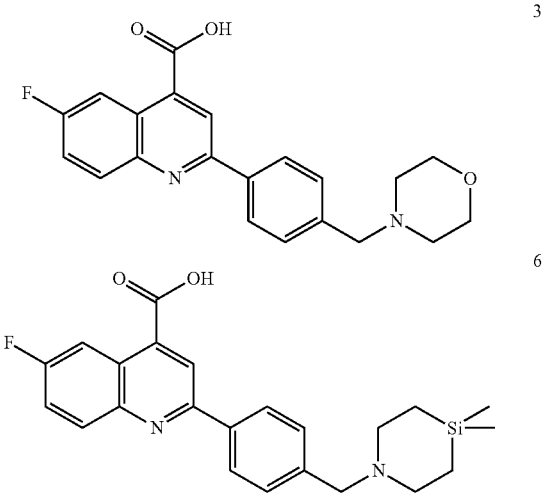

d) adding HATU (1-[Bis(dimethylamino)methylene]-1H-1,2,3-triazolo[4,5-b]pyridinium 3-oxid hexafluorophosphate), DIPEA (N,N-Diisopropylethylamine) and a nitrogen containing heterocyclic compound to a solution of compound 3 or compound 6 obtained in step (c) in a solvent followed by stirring at a temperature in the range of 25 to 30° C. for a period in the range of 10 to 12 h to obtain the silicon incorporated quinoline of formula I.

In a preferred embodiment, the amino compound in step (a) is selected from 4,4-dimethylsilapiperidine or morpholine.

In another preferred embodiment, the nitrogen containing heterocyclic compound in step (d) is selected from the group consisting of 4,4-dimethylsilapiperidine hydrochloride, 2-(4,4-dimethyl-1,4-azasilinan-1-yl)ethan-1-amine hydrochloride, morpholine, 2-morpholinoethan-1-amine, 2-(pyrrolidin-1-yl)ethan-1-amine, and pyridine-2-amine.

In yet another preferred embodiment, the cyano compound in step (a) is 4-(morpholinomethyl)benzonitrile (1) or 4-((4,4-dimethyl-1,4-azasilinan-1-yl)methyl)benzonitrile (4).

In another preferred embodiment, the keto compound in step (b) is 1-(4-(morpholinomethyl) phenyl)ethan-1-one (2) or 1-(4-((4,4-dimethyl-1,4-azasilinan-1-yl)methyl)phenyl) ethan-1-one (5).

In still another preferred embodiment, the acid compound in step (c) is selected from 6-fluoro-2-(4-(morpholinomethyl)phenyl)quinoline-4-carboxylic acid (3) or 2-(4-((4,4-dimethyl-1,4-azasilinan-1-yl)methyl)phenyl)-6-fluoroquinoline-4-carboxylic acid (6).

In yet another embodiment, the present invention provides a pharmaceutical composition comprising a silicon incorporated quinoline of formula I or pharmaceutically acceptable salt thereof and at least one pharmaceutically acceptable carrier.

In still another embodiment, the present invention provides a method for treating diseases caused by *Plasmodium falciparum* or other coccidian parasites, wherein said method comprises administering to a subject a therapeutically effective amount of silicon incorporated quinoline of formula I or pharmaceutically acceptable salt thereof.

DETAILED DESCRIPTION OF THE INVENTION

The invention will now be described in detail in connection with certain preferred and optional embodiments, so that various aspects thereof may be more fully understood and appreciated.

In the view of above, the present invention provides a silicon incorporated quinoline of formula I, and a process for the preparation thereof. The present invention also provides a method for treating diseases caused by *Plasmodium falciparum* or other coccidian parasites, wherein said method comprises administering to a subject a therapeutically effective amount of silicon incorporated quinoline of formula I or pharmaceutically acceptable salt thereof.

In an embodiment, the present invention provides a silicon incorporated quinoline of formula I;

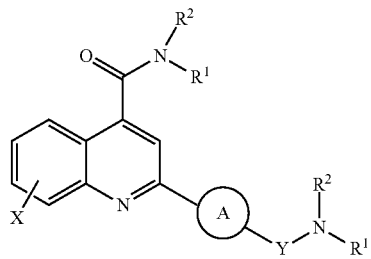

Formula I wherein,

X is selected from the group consisting of hydrogen, halogen, $C_1$-$C_5$ alkyl, $C_1$-$C_5$ haloalkyl, $C_1$-$C_5$ hydroxyalkyl, $C_1$-$C_5$ thioalkyl, and $C_1$-$C_5$ alkoxy;

Y is $CH_2$ or absent;

A is selected from the group consisting of

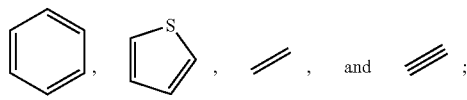

$R^1$ and $R^2$ are independently selected from the group consisting of hydrogen, $C_1$ to $C_{12}$ alkyl, $C_1$-$C_5$ aryl, $C_1$-$C_5$ heteroaryl, $C_1$-$C_5$ aralkyl, $C_1$-$C_5$ hydroxyalkyl, $C_1$-$C_5$ alkoxyalkyl, and $C_1$-$C_5$ aminoalkyl which is optionally substituted or forms a 5 or 6 membered ring which optionally contains an additional hetero atoms selected from the group consisting of O, S, N and Si; and $R^1$ or $R^2$ essentially comprises at least one silicon atom.

In preferred embodiment, the compound of formula I is selected from the group consisting of i. (4,4-dimethyl-1,4-azasilinan-1-yl)(6-fluoro-2-(4-(morpholinomethyl) phenyl) quinolin-4-yl)methanone (NDS 101006), ii. N-(2-(4,4-dimethyl-1,4-azasilinan-1-yl)ethyl)-6-fluoro-2-(4-(morpholinomethyl) phenyl)quinoline-4-carboxamide (NDS 100951), iii. (2-(4-((4,4-dimethyl-1,4-azasilinan-1-yl)methyl)phenyl)-6-fluoroquinolin-4-yl) (morpholino) methanone (NDS 101007), iv. 2-(4-((4,4-dimethyl-1,4-azasilinan-1-yl)methyl)phenyl)-6-fluoro-N-(2-morpholinoethyl)quinoline-4-carboxamide (NDS 101008), v. 2-(4-((4,4-dimethyl-1,4-azasilinan-1-yl)methyl)phenyl)-6-fluoro-N-(2-(pyrrolidin-1-yl)ethyl) quinoline-4-carboxamide (NDS 100950), vi. 2-(4-((4,4-dimethyl-1,4-azasilinan-1-yl)methyl)phenyl)-6-fluoro-N-(pyridin-2-yl) quinoline-4-carboxamide (NDS 101009), vii. 6-fluoro-2-(4-(morpholinomethyl)phenyl)-N-(2-(trimethylsilyl)ethyl)quinoline-4-carboxamide (NDS 101037), viii. 2-(4-((4,4-dimethyl-1,4-azasilinan-1-yl)methyl)phenyl)-6-fluoro-N-(2-(piperidin-1-yl)ethyl)quinoline-4-carboxamide (NDS 101074), ix. 2-(4-((4,4-dimethyl-1,4-azasilinan-1-yl)methyl)phenyl)-6-fluoro-N-(2-(4-methylpiperazin-1-yl)ethyl)quinoline-4-carboxamide (NDS 101075), x. 2-(4-((4,4-dimethyl-1,4-azasilinan-1-yl)methyl)phenyl)-6-fluoro-N-(2-hydroxyethyl)quinoline-4-carboxamide (NDS 101076), and xi. 2-(4-((4,4-dimethyl-1,4-azasilinan-1-yl)methyl)phenyl)-6-fluoro-N-(2-thiomorpholinoethyl)quinoline-4-carboxamide (NDS 101077).

In another embodiment, the present invention provides a process for the preparation of silicon incorporated quinoline of formula I, said process comprising the steps of:

a) adding an amino compound, a base to a solution of 4-(bromomethyl)benzonitrile in a solvent followed by stirring at a temperature in the range of 25 to 30° C. for a period in the range of 10 to 12 h to obtain corresponding cyano compound 1 or compound 4;

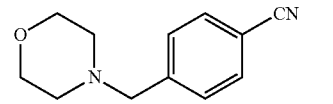

1

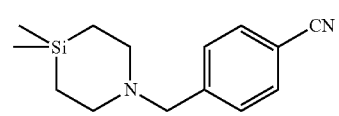

4 b) refluxing a reaction mixture of Grignard reagent and a solution of compound 1 or compound 4 obtained in step (a) in a solvent at a temperature in the range of 100 to 110° C. for a period in the range of 3 to 4 hrs followed by cooling to 0° C. and acidifying with an acid and further refluxing at a temperature in the range of 100 to 110° C. for a period in the range of 1 to 2 h to obtain corresponding keto compound 2 or compound 5;

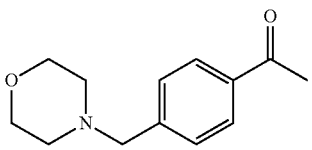

2

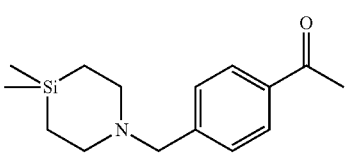

5 c) adding a solvent followed by a base to a reaction mixture of compound 2 or compound 5 obtained in step (b) and 5-fluoroisatin followed by heating the reaction mixture at a temperature in the range of 110 to 120° C. for a period in the range of 10 to 20 min in a microwave reactor to obtain corresponding acid compound 3 or compound 6; and

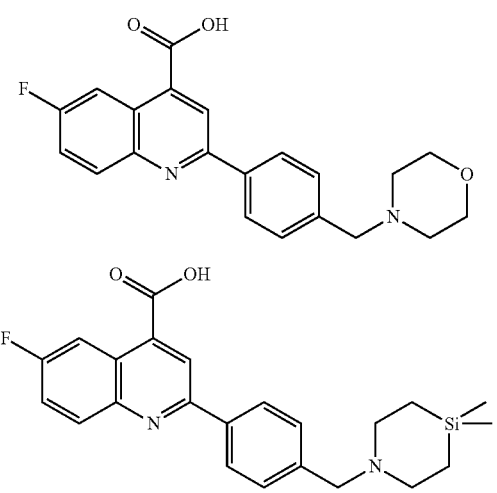

d) adding HATU (1-[Bis(dimethylamino)methylene]-1H-1,2,3-triazolo[4,5-b]pyridinium 3-oxid hexafluorophosphate), DIPEA (N,N-Diisopropylethylamine) and a nitrogen containing heterocyclic compound to a solution of compound 3 or compound 6 obtained in step (c) in a solvent followed by stirring at a temperature in the range of 25 to 30° C. for a period in the range of 10 to 12 h to obtain the silicon incorporated quinoline of formula I.

In a preferred embodiment, the amino compound in step (a) is selected from 4,4-dimethylsilapiperidine or morpholine.

In another preferred embodiment, the nitrogen containing heterocyclic compound in step (d) is selected from the group consisting of 4,4-dimethylsilapiperidine hydrochloride, 2-(4,4-dimethyl-1,4-azasilinan-1-yl)ethan-1-amine hydrochloride, morpholine, 2-morpholinoethan-1-amine, 2-(pyrrolidin-1-yl)ethan-1-amine, and pyridine-2-amine.

In yet another preferred embodiment, the cyano compound in step (a) is 4-(morpholinomethyl)benzonitrile (1) or 4-((4,4-dimethyl-1,4-azasilinan-1-yl)methyl)benzonitrile (4).

In another preferred embodiment, the keto compound in step (b) is 1-(4-(morpholinomethyl)phenyl)ethan-1-one (2) or 1-(4-((4,4-dimethyl-1,4-azasilinan-1-yl)methyl)phenyl)ethan-1-one (5).

In still another preferred embodiment, the acid compound in step (c) is selected from 6-fluoro-2-(4-(morpholinomethyl)phenyl)quinoline-4-carboxylic acid (3) or 2-(4-((4,4-dimethyl-1,4-azasilinan-1-yl)methyl)phenyl)-6-fluoroquinoline-4-carboxylic acid (6).

In another preferred embodiment, the solvent used in step (c) is selected from ethanol, methanol, and water or mixture thereof.

In another preferred embodiment, the base used in step (a) and step (c) is selected from the group consisting of sodium hydroxide, potassium hydroxide, and triethyl amine.

In yet another preferred embodiment, the Grignard reagent is selected from methylmagnesium bromide or methylmagnesiumchloride In still another preferred embodiment, the acid used in step (b) is a mineral acid selected from hydrochloric acid, hydrobromic acid, and sulphuric acid.

In yet still preferred embodiment, the solvent used in step (a), step (b) and step (d) is selected from the group consisting of dichloromethane, toluene, dimethylformamide, acetonitrile, tetrahydrofuran, and diethyl ether.

The process for the preparation of silicon incorporated quinoline of formula I via intermediate 3 is as depicted in the following scheme 1:

Scheme: 1

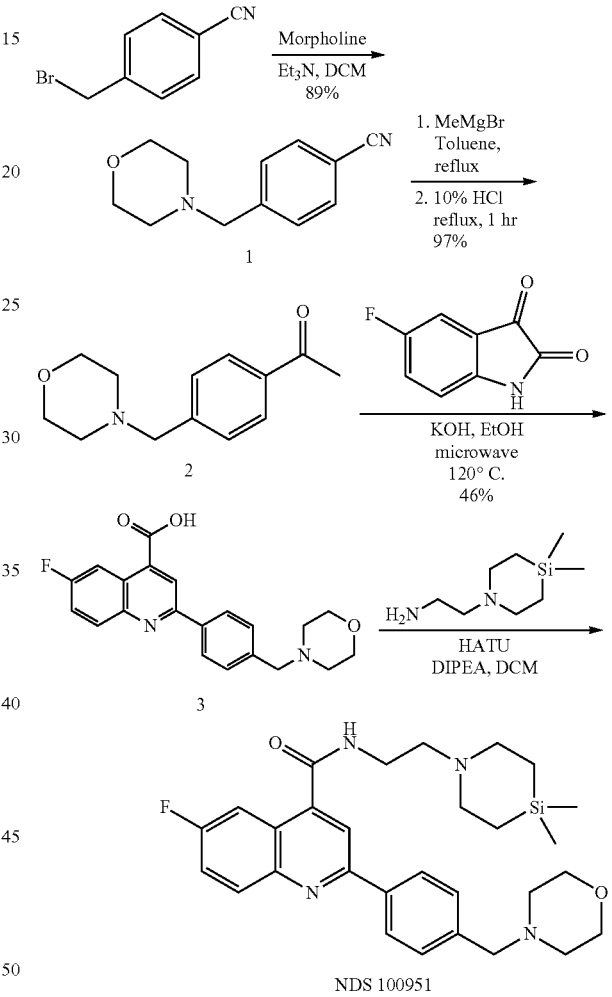

The process for the preparation of silicon incorporated quinoline of formula I via intermediate 6 is as depicted below in scheme 2:

Scheme: 2

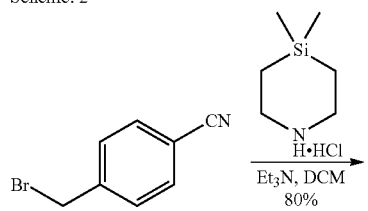

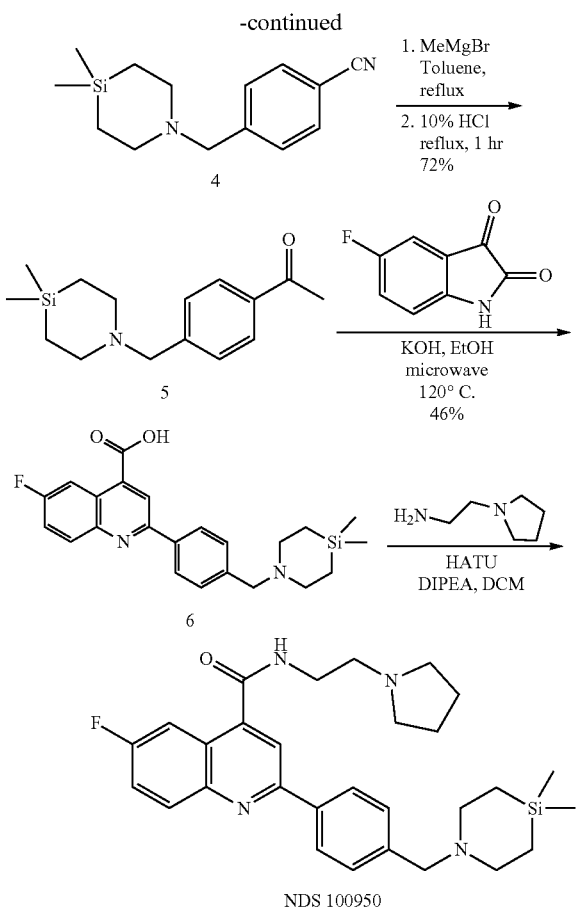

The silicon acid 6 is synthesized by above scheme 2 in which the quinoline core is constructed by a Pfitzinger reaction. The amine 4 is prepared from the commercially available bromo derivative by a displacement reaction. The cyano group is then converted into the methyl ketone 5 by using methyl Grignard followed by hydrolysis of the imine intermediate. This ketone reacted with 5-fluoroisatin in basic medium under microwave conditions to give the quinoline acid 6. The silicon acid 6 is then coupled to different amines under the same conditions (HATU, DIPEA and DCM) and the compounds 2-(4-((4,4-dimethyl-1,4-azasilinan-1-yl) methyl)phenyl)-6-fluoro-N-(2-(pyrrolidin-1-yl)ethyl)quinoline-4-carboxamide (NDS-100950), (2-(4-((4,4-dimethyl-1,4-azasilinan-1-yl)methyl)phenyl)-6-fluoroquinolin-4-yl) (morpholino)methanone (NDS-101007), 2-(4-((4,4-dimethyl-1,4-azasilinan-1-yl)methyl)phenyl)-6-fluoro-N-(2-morpholinoethyl)quinoline-4-carboxamide (NDS-101008), 2-(4-((4,4-dimethyl-1,4-azasilinan-1-yl)methyl) phenyl)-6-fluoro-N-(pyridin-2-yl)quinoline-4-carboxamide (NDS-101009), 6-fluoro-2-(4-(morpholinomethyl)phenyl)-N-(2-(trimethylsilyl)ethyl)quinoline-4-carboxamide (NDS 101037), 2-(4-((4,4-dimethyl-1,4-azasilinan-1-yl)methyl) phenyl)-6-fluoro-N-(2-(piperidin-1-yl)ethyl)quinoline-4-carboxamide (NDS 101074), 2-(4-((4,4-dimethyl-1,4-azasilinan-1-yl)methyl)phenyl)-6-fluoro-N-(2-(4-methylpiperazin-1-yl)ethyl)quinoline-4-carboxamide (NDS 101075), 2-(4-((4,4-dimethyl-1,4-azasilinan-1-yl)methyl) phenyl)-6-fluoro-N-(2-hydroxyethyl)quinoline-4-carboxamide (NDS 101076), and 2-(4-((4,4-dimethyl-1,4-azasilinan-1-yl)methyl)phenyl)-6-fluoro-N-(2-thiomorpholinoethyl)quinoline-4-carboxamide (NDS 101077) are synthesized.

In yet another embodiment, the present invention provides a pharmaceutical composition comprising silicon incorporated quinoline of formula I or pharmaceutically acceptable salt thereof and at least one pharmaceutically acceptable carrier.

The carrier is typically used when the composition is prepared, and includes, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybezoate, talcum, magnesium stearate, mineral oil, or the like.

The composition can additionally comprise stability improving material, viscosity improving or adjusting material, solubility improving material, sweetener, dye, palatability improving material, osmotic pressure variable salt, buffer solution, antioxidant, and so on.

The mode of administration of the pharmaceutical compositions of the present invention can be oral, sublingual, subcutaneous, intramuscular, intravenous, transdermal, local or rectal administration. The active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

The pharmaceutical composition of the present invention contains vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

Solutions comprising compounds of the present invention as free base or pharmacologically acceptable salts can be prepared in water by mixing with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. For parenteral administration in an aqueous solution, for example, the solution should be suitably buffered if necessary and the liquid diluent first rendered isotonic with sufficient saline or glucose.

In accordance with the present invention, the pharmaceutically acceptable salt includes a pharmaceutically acceptable acid addition salt. The pharmaceutically acceptable acid addition salt can be obtained from inorganic acids such as hydrochloric acid, nitric acid, sulfuric acid, hydrobromic acid, hydriodic acid, nitrous acid, or phosphorous acid, and nontoxic organic acids such as aliphatic mono- and dicarboxylates, phenyl-substituted alkanoate, hydroxyl alkanoate, and alkandioate, aromatic acids, and aliphatic and aromatic sulfuric acids.

In another embodiment, the present invention provides a pharmaceutical composition comprising compound of formula (I) or pharmaceutically acceptable salt thereof for preventing and treating malaria and toxoplasmosis comprising administering an effective dose of the pharmaceutical composition to a mammal.

In another preferred embodiment, the present invention provides a pharmaceutical composition comprising compounds of formula (I) or pharmaceutically acceptable salt thereof for the treatment of diseases caused by the pathogens *Plasmodium falciparum* and *Toxoplasma gondii*.

In still another embodiment, the present invention provides a method of treating mammalian malaria, which is characterized by administering an effective dose of pharmaceutical composition to a mammal.

Typically, the pharmaceutical composition of the present invention is administered in the form of a unit dose containing its effective ingredient at an amount between about 1 mg and about 50 mg. The total dose per day of the pharmaceutical composition of the present invention is within a range from about 1 mg to about 50 mg, and preferably from about 1 mg to about 30 mg. However, in comprehensive consideration of the situation of a patient, and in consideration of the activity of an administered medication, a specific dose beyond such a range can be administered. An optimal dose administered under a specific situation must be decided experimentally.

The pharmaceutical composition of the present invention can be administered once or several times at a dose. Preferably, a dose per day is administered once or twice per day. The pharmaceutical composition of the present invention can be administered alone or in conjunction with a pharmaceutically acceptable carrier and excipient. The pharmaceutical composition can be formulated into excipient known in the art as well as a pharmaceutically acceptable carrier and diluents. This formulation can take the form of a unit dose by a method known in the pharmaceutical field for convenience.

The pharmaceutical composition of the present invention can be used in conjunction with one or more other therapeutically useful materials, for instance other anti-malarial drugs.

In one embodiment, the present invention provides a method for treating diseases caused by *Plasmodium falciparum* or other coccidian parasites, wherein said method comprises administering to the subject a therapeutically effective amount of silicon incorporated quinoline of formula (I) or pharmaceutically acceptable salt thereof.

The present invention provides a silicon containing quinoline, which shows significant activity against *Plasmodium falciparum* and another protozoan *Toxoplasma gondii*. By the introduction of Silicon atom, the compounds are expected to have an increase in lipophilicity which can lead to drug candidates with improved brain penetration and can be useful in the treatment of cerebral malaria.

In an aspect, the present invention provides silicon containing quinolone of formula I selected from the group consisting of a. 2-(4-((4,4-dimethyl-1,4-azasilinan-1-yl)methyl)phenyl)-6-fluoro-N-(2-(pyrrolidin-1-yl)ethyl) quinoline-4-carboxamide (NDS 100950);

b. (N-(2-(4,4-dimethyl-1,4-azasilinan-1-yl)ethyl)-6-fluoro-2-(4-(morpholinomethyl) phenyl)quinoline-4-carboxamide (NDS 100951);

c. 2-(4-((4,4-dimethyl-1,4-azasilinan-1-yl)methyl)phenyl)-6-fluoro-N-(pyridin-2-yl) quinoline-4-carboxamide (NDS 101009); and d. 2-(4-((4,4-dimethyl-1,4-azasilinan-1-yl)methyl)phenyl)-6-fluoro-N-(2-(trimethylsilyl)ethyl)quinoline-4-carboxamide (NDS 101037), with more than 20% biological activity against *Toxoplasma gondii*.

In another aspect, the present invention provides silicon containing quinolone of formula I selected from a. 2-(4-((4,4-dimethyl-1,4-azasilinan-1-yl)methyl)phenyl)-6-fluoro-N-(2-(pyrrolidin-1-yl)ethyl) quinoline-4-carboxamide (NDS 100950);

b. (N-(2-(4,4-dimethyl-1,4-azasilinan-1-yl)ethyl)-6-fluoro-2-(4-(morpholinomethyl) phenyl)quinoline-4-carboxamide (NDS 100951);

c. 2-(4-((4,4-dimethyl-1,4-azasilinan-1-yl)methyl)phenyl)-6-fluoro-N-(2-morpholinoethyl)quinoline-4-carboxamide (NDS 101008);

d. 2-(4-((4,4-dimethyl-1,4-azasilinan-1-yl)methyl)phenyl)-6-fluoro-N-(pyridin-2-yl) quinoline-4-carboxamide (NDS 101009);

e. 2-(4-((4,4-dimethyl-1,4-azasilinan-1-yl)methyl)phenyl)-6-fluoro-N-(2-(4-methylpiperazin-1-yl)ethyl)quinoline-4-carboxamide (NDS 101075); and f. 2-(4-((4,4-dimethyl-1,4-azasilinan-1-yl)methyl)phenyl)-6-fluoro-N-(2-thiomorpholinoethyl)quinoline-4-carboxamide (NDS 101077), with more than 90% biological activity against *Plasmodium falciparum*.

In yet another aspect, the present invention provides silicon containing quinolone of formula I a. 2-(4-((4,4-dimethyl-1,4-azasilinan-1-yl)methyl)phenyl)-6-fluoro-N-(2-(pyrrolidin-1-yl)ethyl) quinoline-4-carboxamide (NDS 100950)

with more than 95% biological activity against *Toxoplasma gondii* and *Plasmodium falciparum* respectively.

The biological activity of the selected compounds and prior art compound against *Plasmodium falciparum* and *Toxoplasma gondii* is as shown below in table 1:

TABLE 1

Biological activity of the selected compounds

| Sample Code | (*T. gondii*) | | *P. falciparum* | |
| --- | --- | --- | --- | --- |
| | % Inhibition [@ 10 µM] | EC$_{50}$ (µM) | % Inhibition [@ 10 µM] | EC$_{50}$ (µM) |
| NDS 100950 (Example 8) | 95.2 | 3.94 | 95.7 | 0.06 |
| NDS 100951 (Example 2) | 21.8 | n/d | 93.6 | 0.05 |
| NDS 100949 (Compound lacking Silicon) | 7.2 | n/d | 95.4 | 0.001 |
| NDS 101006 (Example 1) | 0 | n/d | 1.87 | n/d |
| NDS 101007 (Example 6) | 3 | n/d | 2.79 | n/d |
| NDS 101008 (Example 7) | 3 | n/d | 95.9 | 1.26 |
| NDS 101009 (Example 9) | 31 | n/d | 97.1 | 0.81 |
| NDS 101037 (Example 10) | 45 | n/d | 9.16 | n/d |
| NDS 101074 (Example 11) | n/d | n/d | 78.8 | 0.112 |
| NDS 101075 (Example 12) | n/d | n/d | 95.2 | 0.403 |
| NDS 101076 (Example 13) | n/d | n/d | 81.4 | 6.12 |
| NDS 101077 (Example 14) | n/d | n/d | 95.5 | 0.95 |

*n/d - no data available

EXAMPLES

Following examples are given by way of illustration therefore should not be construed to limit the scope of the invention.

Example 1: (4,4-dimethyl-1,4-azasilinan-1-yl)(6-fluoro-2-(4-(morpholinomethyl) phenyl)quinolin-4-yl)methanone (NDS 101006)

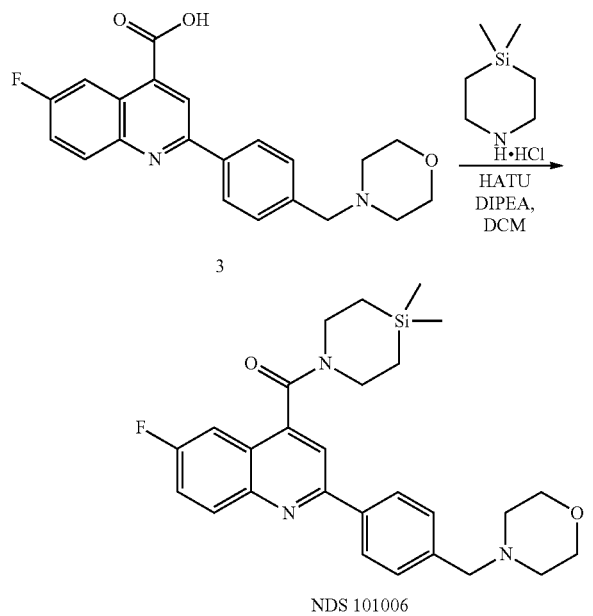

The carboxylic acid 3 was prepared by following procedures known in the literature (*Nature* 2015, 522, 315). To a solution of 3 (110 mg, 0.30 mmol) in dry DCM (6 mL) was added HATU (149 mg, 0.39 mmol), DIPEA (0.2 mL, 1.51 mmol), and 4,4-dimethylsilapiperidine hydrochloride (55 mg, 0.33 mmol) and the reaction mixture was stirred at RT (25-30° C.) for 8-10 h. 2N NaOH was added and the organic layer was separated, dried over Na$_2$SO$_4$ and concentrated in a rotary evaporator. The crude product was purified by column chromatography using 4% MeOH-DCM to give the product as a white solid (80 mg, 56% yield). $^1$H NMR (500 MHz, CDCl$_3$) δ ppm 8.19 (dd, J=5.3, 9.2 Hz, 1H), 8.10 (d, J=8.0 Hz, 2H), 7.81 (s, 1H), 7.61-7.47 (m, 3H), 7.43 (dd, J=2.3, 9.2 Hz, 1H), 4.27 (m, 1H), 3.83 (m, 1H), 3.74 (t, J=4.0 Hz, 4H), 3.60 (s, 2H), 3.41 (t, J=6.3 Hz, 2H), 2.50 (m, 4H), 1.06 (m, 2H), 0.62 (m, 2H), 0.17 (s, 6H); $^{13}$C NMR (125 MHz, CDCl$_3$) δ ppm 167.0, 160.8 (d, J=248.9 Hz), 156.2, 145.6, 143.4, 139.6, 137.9, 132.7 (d, J=9.5 Hz), 129.8, 127.4, 123.9 (d, J=9.5 Hz), 120.5 (d, J=25.8 Hz), 115.9, 108.2 (d, J=22.9 Hz), 67.0, 63.1, 53.6, 46.8, 41.8, 15.5, 13.9, −2.8, −3.4.

Example 2: N-(2-(4,4-dimethyl-1,4-azasilinan-1-yl)ethyl)-6-fluoro-2-(4-(morpholinomethyl)phenyl)quinoline-4-carboxamide (NDS 100951)

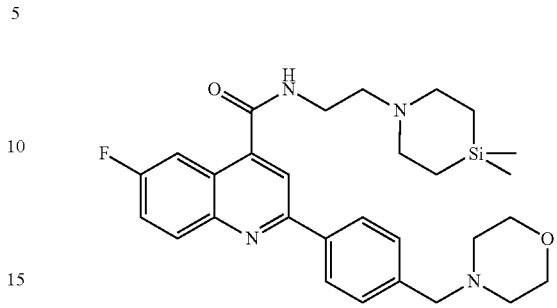

The carboxylic acid 3 was coupled to 2-(4,4-dimethyl-1,4-azasilinan-1-yl)ethan-1-amine hydrochloride by following the same procedure used for the synthesis of NDS 101006. The product was obtained with a yield of 39%. $^1$H NMR (400 MHz, CDCl$_3$) δ ppm 8.33-8.05 (m, 5H), 7.97 (dd, J=10.2, 2.7 Hz, 1H), 7.46 (d, J=7.9 Hz, 3H), 3.87-3.64 (m, 6H), 3.54 (s, 2H), 3.36-3.08 (m, 6H), 2.47 (t, J=4.3 Hz, 4H), 1.05 (t, J=5.9 Hz, 4H), 0.15 (s, 6H); $^{13}$C NMR (100 MHz, CDCl$_3$) δ ppm 168.4, 160.8 (d, J=248.2 Hz), 155.9, 145.9, 140.1, 139.4, 137.4, 132.4 (d, J=10.0 Hz), 129.7, 127.4, 124.1 (d, J=10.8 Hz), 120.1 (d, J=21.6 Hz), 117.9, 109.0 (d, J=23.9 Hz), 66.9, 63.0, 55.6, 53.6, 53.0, 36.0, 11.1, −3.8.

Example 3: 4-((4,4-dimethyl-1,4-azasilinan-1-yl)methyl)benzonitrile (4)

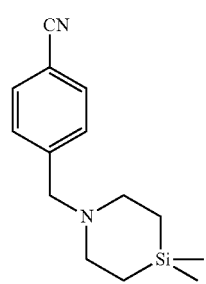 [SMILES: C[Si]1(C)CCN(Cc2ccc(C#N)cc2)CC1]

To a solution of 4-(bromomethyl)benzonitrile (2 g, 10.2 mmol) in dry DCM (40 mL) were added 4,4-dimethylsilapiperidine hydrochloride (2.01 g, 12.2 mmol), triethyl amine (4.3 mL, 30.6 mmol) and stirred at RT (25-30° C.) 8-10 h. Water was added and the organic layer was separated, dried over Na$_2$SO$_4$ and concentrated. The crude was purified by column chromatography using 20-30% Ethylacetate: pet ether to give the pure product (1.97 g, 80% yield). $^1$H NMR (200 MHz, CDCl$_3$) δ ppm 7.62-7.58 (m, 2H), 7.48-7.44 (m, 2H), 3.59 (s, 2H), 2.67 (t, J=6.3 Hz, 4H), 0.76 (t, J=6.3 Hz, 4H), 0.06 (m, 6H); $^{13}$C NMR (50 MHz, CDCl$_3$) δ ppm 145.6, 132.0, 129.2, 119.1, 110.5, 62.4, 52.7, 13.9, −3.1.

Example 4: 1-(4-((4,4-dimethyl-1,4-azasilinan-1-yl)methyl)phenyl)ethan-1-one (5)

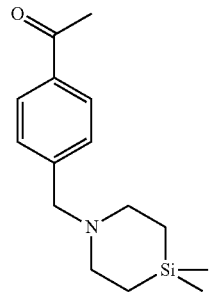 [SMILES: CC(=O)c1ccc(CN2CC[Si](C)(C)CC2)cc1]

Compound 4 (550 mg, 2.25 mmol) was dissolved in dry toluene (10 mL), cooled to 0° C. and methylmagnesium bromide (3M in diethyl ether, 2.3 mL) was added and then refluxed (110° C.) for 4 h. The reaction mixture was cooled to 0° C. and acidified with 10% aqueous HCl and then refluxed for 1 h. The aqueous layer was separated, basified with sat. NaHCO$_3$ and then extracted with DCM, dried and concentrated. This crude product was purified by column chromatography on silica gel using 10% Ethylacetate: pet ether to give the product (410 mg, 70% yield). $^1$H NMR (400 MHz, CDCl$_3$) δ ppm 7.91 (d, J=8.2 Hz, 2H), 7.44 (d, J=8.2 Hz, 3H), 3.61 (s, 2H), 2.69 (t, J=6.4 Hz, 4H), 2.60 (s, 3H), 0.77 (t, J=6.4 Hz, 4H), 0.06 (s, 6H); $^{13}$C NMR (100 MHz, CDCl$_3$) δ ppm 198.0, 145.4, 135.9, 128.8, 128.3, 62.5, 52.7, 26.6, 13.9, −3.1.

Example 5: 2-(4-((4,4-dimethyl-1,4-azasilinan-1-yl)methyl)phenyl)-6-fluoroquinoline-4-carboxylic Acid (6)

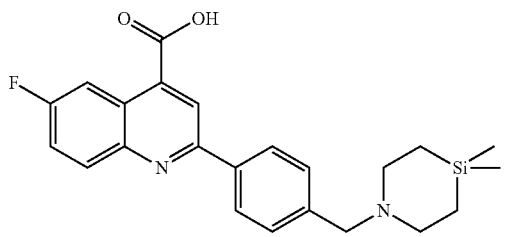 [SMILES: C[Si]1(C)CCN(Cc2ccc(-c3cc(C(=O)O)c4cc(F)ccc4n3)cc2)CC1]

Compound 5 (300 mg, 1.15 mmol) and 5-fluoroisatin (189 mg, 1.15 mmol) was taken in a microwave vial, ethanol (3 mL) and water (3 mL) was added followed by KOH (515 mg, 9.2 mmol). The vial was sealed and heated at 120° C. for 20 min in a microwave reactor. The reaction mixture was cooled and the pH was adjusted to 7 by adding 10% HCl dropwise. The precipitated solid was filtered, washed with water and dried to give the pure product (217 mg, 46% yield). $^1$H NMR (200 MHz, CDCl$_3$) δ ppm 8.11 (dd, J=2.2, 10.7 Hz, 1H), 7.96 (s, 1H), 7.71-7.62 (m, 3H), 7.03 (d, J=7.6 Hz, 2H), 6.95-6.84 (m, 1H), 3.35 (s, 2H), 2.56 (m, 4H), 0.60 (m, 4H), 0.08 (s, 6H).

Example 6: (2-(4-((4,4-dimethyl-1,4-azasilinan-1-yl)methyl)phenyl)-6-fluoroquinolin-4-yl)(morpholino)methanone (NDS 101007)

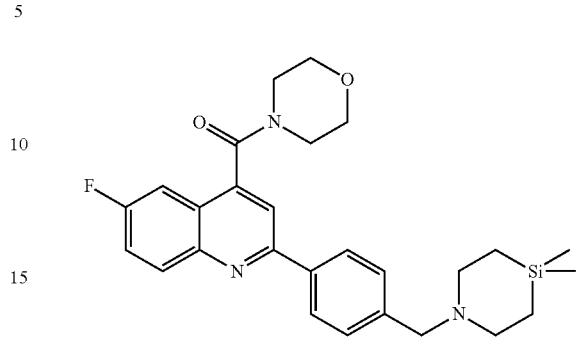

The carboxylic acid 6 was coupled to morpholine by following the same procedure used for the synthesis of NDS 101006. The product was obtained with a yield of 47%. $^1$H NMR (400 MHz, CDCl$_3$) δ ppm 8.20 (dd, J=5.3, 9.0 Hz, 1H), 8.14 (d, J=7.8 Hz, 2H), 7.83 (s, 1H), 7.52-7.62 (m, 3H), 7.42-7.47 (m, 1H), 3.95 (m, 6H), 3.58 (m, 2H), 3.26 (m, 2H), 2.96 (s, 4H), 0.94 (m, 4H), 0.10 (s, 6H), $^{13}$C NMR (100 MHz, CDCl$_3$) δ ppm 166.7, 161.0 (d, J=250.5 Hz), 156.0, 145.6, 142.0, 138.2, 132.9 (d, J=9.2 Hz), 130.4, 127.6, 123.8 (d, J=9.2 Hz), 120.8 (d, J=25.4 Hz), 116.6, 107.9 (d, J=22.4 Hz), 66.9, 66.8, 61.5, 52.4, 47.5, 42.2, 12.6, −3.4.

Example 7: 2-(4-((4,4-dimethyl-1,4-azasilinan-1-yl)methyl)phenyl)-6-fluoro-N-(2-morpholinoethyl)quinoline-4-carboxamide (NDS 101008)

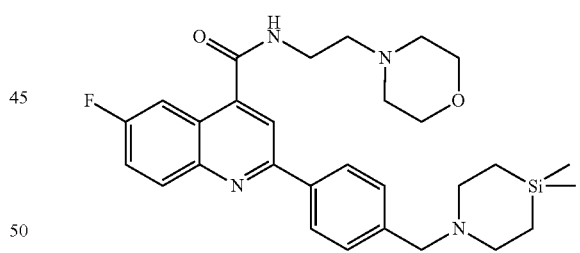

The carboxylic acid 6 was coupled to 2-morpholinoethan-1-amine by following the same procedure used for the synthesis of NDS 101006. The product was obtained with a yield of 32%. $^1$H NMR (400 MHz, CDCl$_3$) δ ppm 8.17 (m, 1H), 8.10 (m, 2H), 7.95 (m, 2H), 7.55 (m, 3H), 6.84 (br.s. 1H), 3.73 (m, 8H), 2.85-2.78 (m, 4H), 2.68 (m, 2H), 2.56 (m, 4H), 0.87 (m, 4H), 0.09 (s, 6H); $^{13}$C NMR (100 MHz, CDCl$_3$) δ ppm 167.1, 161.0 (d, J=248.9 Hz), 155.9, 145.9, 142.2, 139.2, 137.8, 132.5 (d, J=9.2 Hz), 129.9, 127.3, 124.1 (d, J=10.8 Hz), 120.4 (d, J=26.2 Hz), 117.3, 108.8 (d, J=23.9 Hz), 66.8, 61.9, 57.0, 53.4, 52.4, 36.2, 13.1, −3.2.

Example 8: 2-(4-((4,4-dimethyl-1,4-azasilinan-1-yl)methyl)phenyl)-6-fluoro-N-(2-(pyrrolidin-1-yl)ethyl)quinoline-4-carboxamide (NDS 100950)

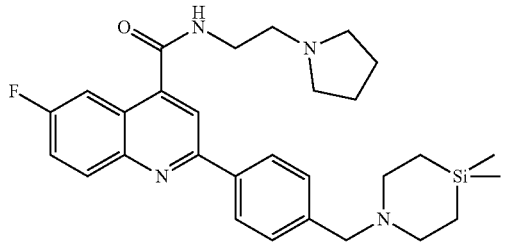 [SMILES: C[Si]1(C)CCN(Cc2ccc(-c3cc(C(=O)NCCN4CCCC4)c4cc(F)ccc4n3)cc2)CC1]

The carboxylic acid 6 was coupled to 2-(pyrrolidin-1-yl)ethan-1-amine by following the same procedure used for the synthesis of NDS 101006. The product was obtained with a yield of 37%. ¹H NMR (400 MHz, CDCl₃) δ ppm 8.35 (br. s., 1H), 8.26-8.22 (m, 3H), 8.14 (dd, J=9.3, 5.6 Hz, 1H), 8.06 (dd, J=10.2, 2.8 Hz, 1H), 7.58 (d, J=8.1 Hz, 2H), 7.53-7.48 (m, 1H), 3.88-3.64 (m, 5H), 3.19 (t, J=5.5 Hz, 2H), 3.10 (m, 4H), 2.98 (t, J=5.9 Hz, 4H), 2.02 (m, 4H), 0.98 (t, J=6.2 Hz, 4H), 0.11 (m, 6H).

Example 9: 2-(4-((4,4-dimethyl-1,4-azasilinan-1-yl)methyl)phenyl)-6-fluoro-N-(pyridin-2-yl)quinoline-4-carboxamide (NDS 101009)

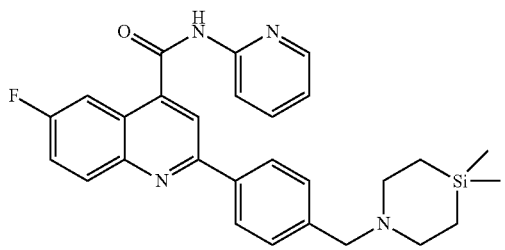 [SMILES: C[Si]1(C)CCN(Cc2ccc(-c3cc(C(=O)Nc4ccccn4)c4cc(F)ccc4n3)cc2)CC1]

The carboxylic acid 6 was coupled to pyridine-2-amine by following the same procedure used for the synthesis of NDS 101006. The product was obtained with a yield of 21%. ¹H NMR (400 MHz, CDCl₃) δ ppm 9.50 (br. s., 1H), 8.44 (d, J=8.3 Hz, 1H), 8.20 (dd, J=9.0, 5.6 Hz, 1H), 8.05-8.02 (m, 4H), 7.92 (m, 1H), 7.78 (t, J=7.6 Hz, 1H), 7.56-7.50 (m, 3H), 7.04 (t, J=5.6 Hz, 1H), 3.75 (s, 2H), 2.84 (t, J=5.4 Hz, 4H), 0.86 (t, J=5.9 Hz, 4H), 0.08 (s, 6H); ¹³C NMR (100 MHz, CDCl₃) δ ppm 165.5, 161.1 (d, J=249.7 Hz), 155.8, 151.1, 147.8, 146.0, 141.2, 141.1, 138.7, 137.3, 132.6 (d, J=9.2 Hz), 129.9, 127.2, 123.9 (d, J=10.8 Hz), 120.7 (d, J=25.4 Hz), 120.6, 117.2, 114.6, 108.8 (d, J=23.9 Hz), 62.1, 52.5, 13.3, −3.2.

Example 10: 2-(4-((4,4-dimethyl-1,4-azasilinan-1-yl)methyl)phenyl)-6-fluoro-N-(2-(trimethylsilyl)ethyl)quinoline-4-carboxamide (NDS 101037)

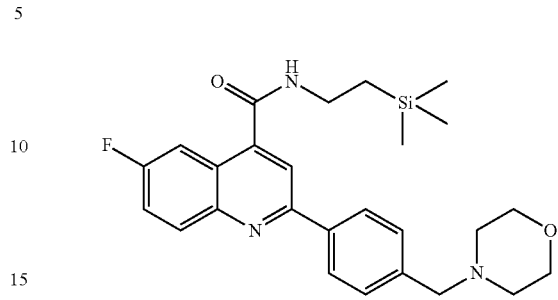

The carboxylic acid 3 was coupled to 2-(trimethylsilyl)ethan-1-amine by following the same procedure used for the synthesis of NDS 101006. The product was obtained with a yield of 40%. ¹H NMR (400 MHz, CDCl₃) δ ppm 8.17-8.14 (m, 1H), 8.06 (d, J=6.4 Hz, 2H), 7.88-7.86 (m, 2H), 7.54-7.48 (m, 3H), 6.13 (br. s., 1H), 3.73 (t, J=4.4 Hz, 4H), 3.63-3.59 (m, 4H), 2.49 (m, 4H), 1.01-0.97 (m, 2H), 0.11 (s, 9H); HRMS (ESI): m/z calculated for C₂₆H₃₃FN₃O₂Si [M+H]+466.2248 found 466.2320.

Example 11: 2-(4-((4,4-dimethyl-1,4-azasilinan-1-yl)methyl)phenyl)-6-fluoro-N-(2-(piperidin-1-yl)ethyl)quinoline-4-carboxamide (NDS 101074)

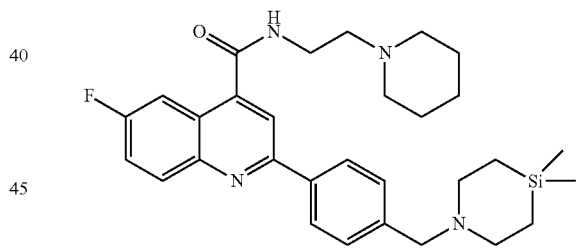

The carboxylic acid 6 was coupled to 2-(piperidin-1-yl)ethan-1-amine by following the same procedure used for the synthesis of NDS 101006. The product was obtained with a yield of 26%. ¹H NMR (400 MHz, CDCl₃) δ ppm 8.28-8.12 (m, 3H), 8.05-7.98 (m, 2H), 7.66 (m, 1H), 7.52 (m, 3H), 3.76 (m, 4H), 2.85 (m, 4H), 2.79 (m, 2H), 2.65 (m, 4H), 1.68 (m, 4H), 1.50 (m, 2H), 0.87 (m, 4H), 0.07 (s, 6H); ¹³C NMR (100 MHz, CDCl₃) δ ppm 167.2, 161.0 (d, J=248.9 Hz), 156.0, 146.0, 141.7, 138.6, 138.0, 132.4 (d, J=10.0 Hz), 130.0, 127.5, 124.3 (d, J=10.0 Hz), 120.3 (d, J=25.4 Hz), 117.7, 109.0 (d, J=23.9 Hz), 61.8, 57.0, 54.2, 52.4, 36.1, 24.9, 23.7, 13.0, −3.3; HRMS (ESI): m/z calculated for C₃₀H₄₀FN₄OSi [M+H]⁺519.287, found 519.2957.

Example 12: 2-(4-((4,4-dimethyl-1,4-azasilinan-1-yl)methyl)phenyl)-6-fluoro-N-(2-(4-methylpiperazin-1-yl)ethyl)quinoline-4-carboxamide (NDS 101075)

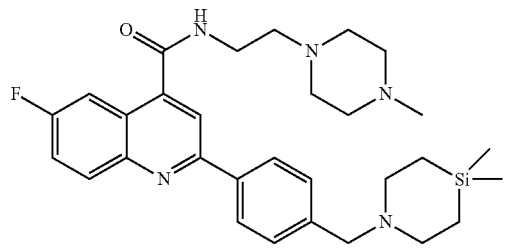 [SMILES: CN1CCN(CCNC(=O)c2cc(-c3ccc(CN4CC[Si](C)(C)CC4)cc3)nc3ccc(F)cc23)CC1]

The carboxylic acid 4 was coupled to 2-(4-methylpiperazin-1-yl)ethan-1-amine by following the same procedure used for the synthesis of NDS 101006. The product was obtained with a yield of 38%. $^1$H NMR (400 MHz, CDCl$_3$) δ ppm 8.19-8.09 (m, 3H), 7.98-7.95 (m, 2H), 7.56-7.49 (m, 3H), 6.82 (m, 1H), 3.75 (s, 2H), 3.67 (q, J=5.4 Hz, 2H), 2.83 (m, 4H), 2.68 (t, J=5.9 Hz, 2H), 2.61-2.50 (m, 8H), 2.30 (s, 3H), 0.86 (m, 4H), 0.07 (s, 6H); $^{13}$C NMR (100 MHz, CDCl$_3$) δ ppm 167.0, 160.9 (d, J=248.2 Hz), 156.0, 146.0, 142.3, 142.2, 137.9, 132.6 (d, J=9.2 Hz), 130.0, 127.4, 124.2 (d, J=10.0 Hz), 120.4 (d, J=25.4 Hz), 117.4, 108.9 (d, J=23.9 Hz), 61.9, 56.2, 54.9, 52.6, 52.4, 45.8, 36.5, 13.1, −3.2; HRMS (ESI): m/z calculated for C$_{30}$H$_{41}$FN$_5$OSi [M+H]$^+$ 534.2986, found 534.3064.

Example 13: 2-(4-((4,4-dimethyl-1,4-azasilinan-1-yl)methyl)phenyl)-6-fluoro-N-(2-hydroxyethyl)quinoline-4-carboxamide (NDS 101076)

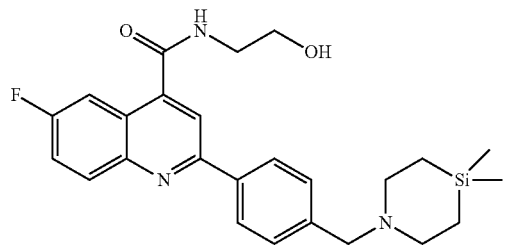 [SMILES: C[Si]1(C)CCN(Cc2ccc(-c3cc(C(=O)NCCO)c4cc(F)ccc4n3)cc2)CC1]

The carboxylic acid 6 was coupled to ethanolamine by following the same procedure used for the synthesis of NDS 101006. The product was obtained with a yield of 30%. $^1$H NMR (400 MHz, CDCl$_3$) δ ppm 8.06 (dd, J=5.4, 9.3 Hz, 1H), 7.95 (d, J=7.8 Hz, 2H), 7.79-7.76 (m, 2H), 7.46-7.42 (m, 3H), 7.06 (m, 1H), 3.87 (t, J=4.9 Hz, 2H), 3.70-3.65 (m, 4H), 2.77 (t, J=6.1 Hz, 4H), 0.80 (t, J=6.1 Hz, 4H), 0.06 (s, 6H); $^{13}$C NMR (100 MHz, CDCl$_3$) δ ppm 167.8, 160.8 (d, J=249.7 Hz), 155.8, 145.7, 141.7, 141.6, 137.3, 132.3 (d, J=9.2 Hz), 129.7, 127.2, 124.2 (d, J=10.0 Hz), 120.4 (d, J=25.4 Hz), 117.1, 108.9 (d, J=23.9 Hz), 62.0, 61.6, 52.4, 42.7, 13.3, −3.2; HRMS (ESI): m/z calculated for C$_{25}$H$_{31}$FN$_3$O$_2$Si [M+H]$^+$ 452.2091, found 452.2169.

Example 14: 2-(4-((4,4-dimethyl-1,4-azasilinan-1-yl)methyl)phenyl)-6-fluoro-N-(2-thiomorpholinoethyl)quinoline-4-carboxamide (NDS 101077)

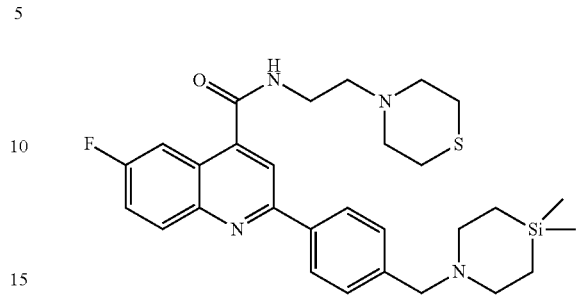

The carboxylic acid 6 was coupled to 2-thiomorpholinoethan-1-amine by following the same procedure used for the synthesis of NDS 101006. The product was obtained with a yield of 40%. $^1$H NMR (400 MHz, CDCl$_3$) δ ppm 8.19 (dd, J=5.5, 8.5 Hz, 1H), 8.11 (d, J=7.9 Hz, 2H), 7.96-7.93 (m, 2H), 7.58-7.51 (m, 3H), 6.71 (m, 1H), 3.80 (s, 2H), 3.67 (q, J=5.5 Hz, 2H), 2.89 (m, 4H), 2.83-2.81 (m, 4H), 2.70-2.60 (m, 6H), 0.90 (m, 4H), 0.09 (s, 6H); HRMS (ESI): m/z calculated for C$_{29}$H$_{38}$FN$_4$OSSi [M+H]$^+$537.2441, found 537.2519.

Example 15: Protocol for Anti-Malarial and Anti-Toxoplasma Bioactivity Screening a) Anti-malarial screening: *Plasmodium falciparum* (3D7; Malaria Research and Reference Reagent Resource Center ID NO: MRA-102) is cultured in the laboratory as per standard protocols [Moll et. al. 2008]. Briefly, *P. falciparum* is cultured using 2% hematocrit washed RBCs, separated from freshly collected human blood, in RPMI media containing glutamine, sodium bicarbonate and antibiotics. Parasites are routinely synchronized using 5% sorbitol treatment. Anti-malarial screens are carried out in two stages: 1) a primary screen at a fixed concentration of 10 μM to find out % inhibition of growth; and 2) a dose assay for finding out the IC$_{50}$ of hits identified from the primary screen. In both assays the following steps are followed. 200 μL's of the diluted parasite culture (2% parasitemia and 2% hematocrit; at late ring stage), is added to each well in a 96 well plate pre-seeded with the compound of interest at the required concentration of 10 μM. The master stocks and dilutions of the compounds are prepared in cell culture grade DMSO. NOTE: DMSO only treatment control is done and the results are used for normalizing the data obtained from compound treatment. All compounds are plated in triplicates. Each 96 well plate also includes negative control (compound untreated culture) and positive control (standard anti-malarial treated culture). Standard anti-malarials used are chloroquine, artemisinine and atovaquone, each at 1 μM concentration. After plating, the culture is incubated in standard growth condition for 60 hours, after which the cultures are processed for testing the effect of compounds on parasite growth using SybrGreen staining and fluorescence measurements at 520 nM emission following excitation at 498 nM. Since only the parasites have DNA (as RBCs are devoid of nucleus), the SybrGreen signal is a direct indictor of parasite density in respective samples. Results are used to quantifying relative parasite growth (or conversely % inhibition of growth) in untreated, standard anti-malarial treated and test molecules treated *P. falciparum* cultures. Compounds showing greater than 80% reduction in parasitemia are selected from this primary screening for carrying out dose response analysis using the respective test molecules from 10 μM to 1 nM dilution series. Data from this experiment is used for the calculation of $IC_{50}$ values for the respective test molecules.

b) Anti-toxoplasma screening: For screening bioactivity of test molecules against *T. gondii*, a transgenic line of the parasite expressing the luciferase gene is used. The parental parasite used to generate the TgLuc+ strain is a Type I (RH) virulent strain (ATCC reference 50174D), which can also be used for in vivo studies in mice, if needed. The tachyzoite stage of the parasites are routinely cultured in the laboratory using standard protocols [Roos et al., 1994. In brief, a confluent monolayer of Human Foreskin Fibroblast (HFF; ATCC reference SCRS-1041) cells in culture are used as the host cells for infection with tachyzoite stage *T. gondii*. The culture media used to grow parasites is standard complete DMEM (Gibco BRL, USA) containing glucose (5.5 mM), glutamine (2 mM), Hepes (25 mM) and 1% dialyzed bovine fetal calf serum (Gibco BRL, USA). For bioactivity assays, the HFF cells are grown in 96 well plates and each well is infected with $1 \times 10^4$ TgLuc+ parasitesin the presence of 10 μM of test molecules (in primary screens) in a total volume of 200 μL. After 2 days of incubation and growth in a 37° C. incubator maintaining 5% $CO_2$, the 96 well plates are processed for luminescence measurements using the reagents in the luciferase assay kit (Promega, USA). The results are corrected for background (uninfected HFF cultures), and normalized against both positive (untreated parasite cultures) and negative (standard drug treated parasite cultures) to identify those molecules with % inhibition values >80% for further dose analysis using the respective test molecules from 10 μM to 1 nM dilution series. Data from this experiment is used for the calculation of $IC_{50}$ values for the respective test molecules. Data from the preliminary screen (@ 10 μM only) is shown in Table-1 and dose response experiments are underway.

TABLE 1

Biological activity of the selected compounds

| | (*T. gondii*) | | *P. falciparum* | |
|---|---|---|---|---|
| Sample Code | % Inhibition [@ 10 μM] | $EC_{50}$ (μM) | % Inhibition [@ 10 μM] | $EC_{50}$ (μM) |
| NDS 100950 (Example 8) | 95.2 | 3.94 | 95.7 | 0.06 |
| NDS 100951 (Example 2) | 21.8 | n/d | 93.6 | 0.05 |
| NDS 100949 (Compound lacking Silicon) | 7.2 | n/d | 95.4 | 0.001 |
| NDS 101006 (Example 1) | 0 | n/d | 1.87 | n/d |
| NDS 101007 (Example 6) | 3 | n/d | 2.79 | n/d |
| NDS 101008 (Example 7) | 3 | n/d | 95.9 | 1.26 |
| NDS 101009 (Example 9) | 31 | n/d | 97.1 | 0.81 |
| NDS 101037 (Example 10) | 45 | n/d | 9.16 | n/d |
| NDS 101074 (Example 11) | n/d | n/d | 78.8 | 0.112 |
| NDS 101075 (Example 12) | n/d | n/d | 95.2 | 0.403 |

TABLE 1-continued

Biological activity of the selected compounds

| | (*T. gondii*) | | *P. falciparum* | |
|---|---|---|---|---|
| Sample Code | % Inhibition [@ 10 μM] | $EC_{50}$ (μM) | % Inhibition [@ 10 μM] | $EC_{50}$ (μM) |
| NDS 101076 (Example 13) | n/d | n/d | 81.4 | 6.12 |
| NDS 101077 (Example 14) | n/d | n/d | 95.5 | 0.95 |

*n/d - no data available

Example 16: Formulation Details

| Drug | 10.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Then the active ingredient and Magnesium stearate was mixed and filled in a sample vial. Mode of administration: Disperse the powder in water/juice.

Example 17: Formulation Details

| Drug | 10.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Then the active ingredient and Magnesium stearate was mixed and filled in a sample vial. Mode of administration: Disperse the powder in water/juice.

Advantages of the Invention a. Novel compounds useful in treating diseases caused by *Plasmodium falciparum* and other coccidian parasites.
b. Silicon compounds are useful in the treatment of cerebral malaria.

We claim:
1. A silicon incorporated quinoline of formula I

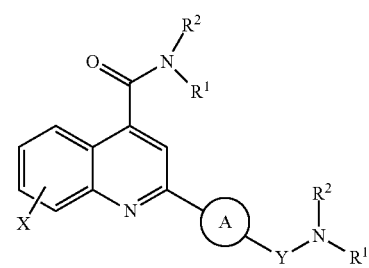

Formula I wherein,
X is halogen;
Y is CH₂ or absent;
A is

R¹ and R² are independently selected from the group consisting of hydrogen, C₁ to C₁₂ alkyl, C₁-C₅ aryl, C₁-C₅ heteroaryl, C₁-C₅ aralkyl, C₁-C₅ hydroxyalkyl, C₁-C₅ alkoxyalkyl, and C₁-C₅aminoalkyl which is optionally substituted or forms a 5 or 6 membered ring which optionally contains an additional hetero atoms selected from the group consisting of O, S, N and Si; and R¹ or R² essentially comprises at least one silicon atom.

2. The compound of formula I as claimed in claim 1, wherein said compound of formula I is selected from the group consisting of:
 a. (4,4-dimethyl-1,4-azasilinan-1-yl)(6-fluoro-2-(4-(morpholinomethyl)phenyl) quinolin-4-yl)methanone (NDS 101006);
 b. N-(2-(4,4-dimethyl-1,4-azasilinan-1-yl)ethyl)-6-fluoro-2-(4-(morpholinomethyl) phenyl)quinoline-4-carboxamide (NDS 100951);
 c. (2-(4-((4,4-dimethyl-1,4-azasilinan-1-yl)methyl)phenyl)-6-fluoroquinolin-4-yl) (morpholino) methanone (NDS 101007);
 d. 2-(4-(4,4-dimethyl-1,4-azasilinan-1-yl)methyl)phenyl)-6-fluoro-N-(2-morpholinoethyl)quinoline-4-carboxamide (NDS 101008);
 e. 2-(4-(4,4-dimethyl-1,4-azasilinan-1-yl)methyl)phenyl)-6-fluoro-N-(2-(pyrrolidin-1-yl)ethyl) quinoline-4-carboxamide (NDS 100950);
 f. 2-(4-((4,4-dimethyl-1,4-azasilinan-1-yl)methyl)phenyl)-6-fluoro-N-(pyridin-2-yl) quinoline-4-carboxamide (NDS 101009);
 g. 6-fluoro-2-(4-(morpholinomethyl)phenyl)-N-(2-(trimethylsilyl)ethyl)quinoline-4-carboxamide (NDS 101037);
 h. 2-(4-((4,4-dimethyl-1,4-azasilinan-1-yl)methyl)phenyl)-6-fluoro-N-(2-(piperidin-1-yl)ethyl)quinoline-4-carboxamide (NDS 101074);
 i. 2-(4-((4,4-dimethyl-1,4-azasilinan-1-yl)methyl)phenyl)-6-fluoro-N-(2-(4-methylpiperazin-1-yl)ethyl)quinoline-4-carboxamide (NDS 101075);
 j. 2-(4-((4,4-dimethyl-1,4-azasilinan-1-yl)methyl)phenyl)-6-fluoro-N-(2-hydroxyethyl)quinoline-4-carboxamide (NDS 101076); and
 k. 2-(4-((4,4-dimethyl-1,4-azasilinan-1-yl)methyl)phenyl)-6-fluoro-N-(2-thiomorpholinoethyl)quinoline-4-carboxamide (NDS 101077).

3. A process for the preparation of silicon incorporated quinoline of formula (I), said process comprises the steps of:
 a) adding an amino compound selected from 4,4-dimethylsilapiperidine or morpholine and a base to a solution of 4-(bromomethyl)benzonitrile in a solvent followed by stirring at a temperature in the range of 25 to 30° C. for a period in the range of 10 to 12 h to obtain corresponding cyano compound 1 (4-morpholinomethyl)benzonitrile) or compound 4 (4-((4,4-dimethyl-1,4-azasilinan-1-yl)methyl)benzonitrile);

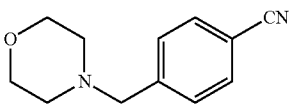

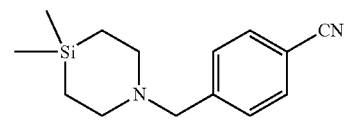

b) refluxing a reaction mixture of a Grignard reagent and a solution of compound 1 or 4 obtained in step (a) in a solvent at a temperature in the range of 100 to 110° C. for a period in the range of 3 to 4 hrs followed by cooling to 0° C. and acidifying with an acid and further refluxing at a temperature in the range of 100 to 110° C. for a period in the range of 1 to 2 h to obtain corresponding keto compound 2 (1-(4-(morpholinomethyl)phenyl)ethan-1-one) or compound 5 (1-(4-((4,4-dimethyl-1,4-azasilinan-1-yl)methyl)phenyl)ethan-1-one);

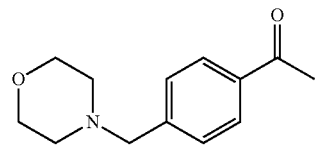

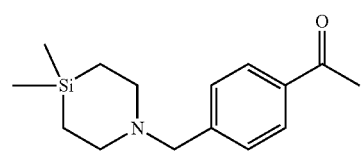

c) adding a solvent followed by a base to a reaction mixture of compound 2 or compound 5 obtained in step (b) and 5-fluoroisatin followed by heating the reaction mixture at a temperature in the range of 110 to 120° C. for a period in the range of 10 to 20 min in a microwave reactor to obtain corresponding acid compound 3 (6-fluoro-2-(4(morpholinomethyl)phenyl)quinolone-4-carboxylic acid) or compound 6 (2-(4-((4,4-dimethyl-1,4-azasilinan-1-yl)methyl)phenyl)-6-fluoroquinoline-4-carboxylic acid);

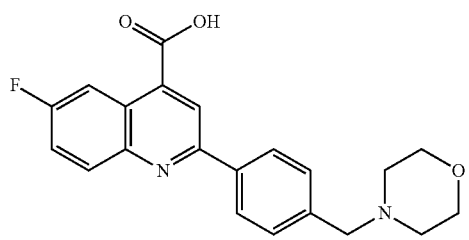

-continued

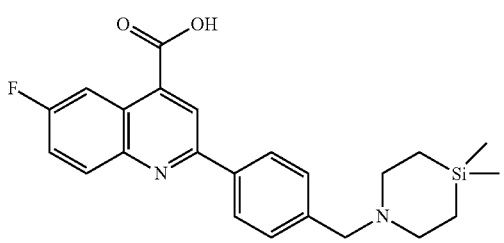

6 d) adding HATU (1-[Bis(dimethylamino)methylene]-1H-1,2,3-triazolo[4,5-b]pyridinium 3-oxid hexafluorophosphate), DIPEA (N,N-Diisopropylethylamine) and a nitrogen containing heterocyclic compound to a solution of compound 3 or compound 6 obtained in step (c) in a solvent followed by stirring at a temperature in the range of 25 to 30° C. for a period in the range of 10 to 12 h to obtain the silicon incorporated quinoline of formula I.

4. The process as claimed in claim 3, wherein the nitrogen containing heterocyclic compound in step (d) is selected from the group consisting of 4,4-dimethylsilapiperidine hydrochloride, 2-(4,4-dimethyl-1,4-azasilinan-1-yl)ethan-1-amine hydrochloride, morpholine, 2-morpholinoethan-1-amine, 2-(pyrrolidin-1-yl)ethan-1-amine, and pyridine-2-amine.

5. The process as claimed in claim 3, wherein the solvent in step (c) is selected from the group consisting of ethanol, methanol, and water or mixture thereof.

6. The process as claimed in claim 3, wherein the base in step (a) and step (c) is selected from the group consisting of sodium hydroxide, potassium hydroxide and triethyl amine.

7. The process as claimed in claim 3, wherein the Grignard reagent in step (b) selected from methylmagnesium bromide or methylmagnesium chloride.

8. The process as claimed in claim 3, wherein the acid in step (b) is a mineral acid selected from the group consisting of hydrochloric acid, hydrobromic acid, and sulphuric acid.

9. The process as claimed in claim 3, wherein the solvent in step (a), step (b) and step (d) is selected from the group consisting of dichloromethane, toluene, dimethylformamide, acetonitrile, tetrahydrofuran, and diethyl ether.

10. A pharmaceutical composition comprising the silicon incorporated quinolines of formula I or pharmaceutically acceptable salt thereof and at least one pharmaceutically acceptable carrier Formula I

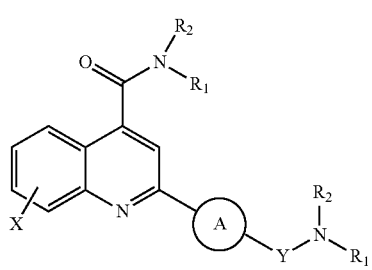

wherein,
X is halogen;
Y is $CH_2$ or absent;
A is

.

$R^1$ and $R^2$ are independently selected from the group consisting of hydrogen, $C_1$ to $C_{12}$ alkyl, $C_1$-$C_5$ aryl, $C_1$-$C_5$ heteroaryl, $C_1$-$C_5$ aralkyl, $C_1$-$C_5$ hydroxyalkyl, $C_1$-$C_5$ alkoxyalkyl, and $C_1$-$C_5$ aminoalkyl which is optionally substituted or forms a 5 or 6 membered ring which optionally contains an additional hetero atoms selected from the group consisting of O, S, N and Si; and
$R^1$ or $R^2$ essentially comprises at least one silicon atom.

11. A method for treating diseases caused by *Plasmodium falciparum* or other coccidian parasites, said method comprising administering to a subject a therapeutically effective amount of silicon incorporated quinolines of formula I or pharmaceutically acceptable salt thereof Formula I

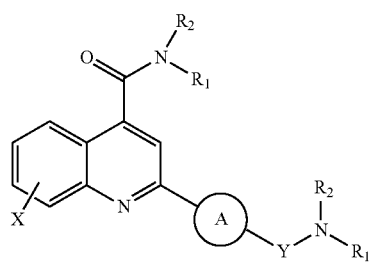

wherein,
X is halogen;
Y is $CH_2$ or absent;
A is

.

$R^1$ and $R^2$ are independently selected from the group consisting of hydrogen, $C_1$ to $C_{12}$ alkyl, $C_1$-$C_5$ aryl, $C_1$-$C_5$ heteroaryl, $C_1$-$C_5$ aralkyl, $C_1$-$C_5$ hydroxyalkyl, $C_1$-$C_5$ alkoxyalkyl, and $C_1$-$C_5$ aminoalkyl which is optionally substituted or forms a 5 or 6 membered ring which optionally contains an additional hetero atoms selected from the group consisting of O, S, N and Si; and
$R^1$ or $R^2$ essentially comprises at least one silicon atom.

* * * * *